United States Patent
Mansouri et al.

(10) Patent No.: US 7,238,363 B2
(45) Date of Patent: Jul. 3, 2007

(54) MODIFICATION OF MEDICAL PROSTHESES

(75) Inventors: Mohammad D. Mansouri, Houston, TX (US); Rabih O. Darouiche, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 220 days.

(21) Appl. No.: 11/095,975

(22) Filed: Mar. 31, 2005

(65) Prior Publication Data

US 2005/0271694 A1    Dec. 8, 2005

Related U.S. Application Data

(60) Provisional application No. 60/558,918, filed on Apr. 2, 2004.

(51) Int. Cl.
*A61F 2/00* (2006.01)
*A61L 33/00* (2006.01)

(52) U.S. Cl. ..................... 424/423; 427/2.24
(58) Field of Classification Search .............. 424/423; 427/2.1, 2.12, 2.13, 2.24, 2.25
See application file for complete search history.

(56) References Cited

U.S. PATENT DOCUMENTS

| | | | |
|---|---|---|---|
| 3,954,467 A | 5/1976 | Takimoto et al. | |
| 4,107,121 A | 8/1978 | Stoy | |
| 4,207,313 A | 6/1980 | Umezawa et al. | |
| 4,306,563 A | 12/1981 | Iwatschenko | |
| 4,341,768 A | 7/1982 | Konishi et al. | |
| 4,423,153 A | 12/1983 | Ranney et al. | |
| 4,442,133 A | 4/1984 | Greco et al. | |
| 4,769,013 A | 9/1988 | Lorenz et al. | |
| 4,895,566 A | 1/1990 | Lee | |
| 4,917,686 A | 4/1990 | Bayston et al. | |
| 4,952,419 A | 8/1990 | De Leon et al. | |
| 5,013,306 A | 5/1991 | Solomon et al. | |
| 5,197,977 A | 3/1993 | Hoffman, Jr. et al. | |
| 5,217,493 A | 6/1993 | Raad et al. | |
| 5,357,636 A * | 10/1994 | Dresdner et al. | 2/161.7 |
| 5,369,155 A | 11/1994 | Asmus | |
| 5,498,416 A | 3/1996 | Carsenti-Etesse et al. | |
| 5,507,777 A | 4/1996 | Kus et al. | |
| 5,616,338 A | 4/1997 | Fox et al. | |
| 5,624,704 A | 4/1997 | Darouiche et al. | |
| 5,628,785 A | 5/1997 | Schwartz et al. | |
| 5,705,092 A | 1/1998 | Wellinghoff et al. | |
| 5,756,145 A | 5/1998 | Darouiche | |
| 5,830,539 A | 11/1998 | Yan et al. | |
| 5,853,745 A | 12/1998 | Darouiche | |
| 5,902,283 A | 5/1999 | Darouiche | |
| 5,939,208 A | 8/1999 | Stoy | |
| 6,008,195 A | 12/1999 | Selsted | |
| 6,054,504 A | 4/2000 | Dalla Riva Toma | |
| 6,096,369 A | 8/2000 | Anders et al. | |
| 6,162,487 A | 12/2000 | Darouiche | |
| 6,166,007 A | 12/2000 | Sodemann | |
| 6,172,163 B1 | 1/2001 | Rein et al. | |
| 6,322,847 B1 | 11/2001 | Zhong et al. | |
| 6,444,234 B1 | 9/2002 | Kirby et al. | |
| 6,589,591 B1 | 7/2003 | Mansouri et al. | |
| 6,719,991 B2 | 4/2004 | Darouiche et al. | |
| 2003/0229401 A1 | 12/2003 | Mansouri et al. | |
| 2004/0166094 A1 | 8/2004 | Darouiche et al. | |
| 2004/0166102 A1 | 8/2004 | Darouiche et al. | |

FOREIGN PATENT DOCUMENTS

| | | |
|---|---|---|
| JP | 61179162 | 8/1986 |
| WO | WO-96/33670 | 10/1996 |
| WO | WO-00/72896 | 12/2000 |
| WO | WO-01/95876 | 12/2001 |
| WO | WO-03/006179 | 1/2003 |

OTHER PUBLICATIONS

U.S. Appl. No. 10/463,062, filed Jun. 18, 2003.*

* cited by examiner

*Primary Examiner*—Sharon Kennedy
(74) *Attorney, Agent, or Firm*—Fulbright & Jaworski LLP

(57) ABSTRACT

The incorporation of one or more therapeutic agents on metallic and non-metallic medical prostheses is provided. The therapeutic agent can be used, for example, to prevent, treat, or reduce bacterial and fungal infections associated with these implants. Additionally, the therapeutic agents can be used to effect other therapeutic benefits. Specifically, a bilayer therapeutic coating is applied in two steps. Additionally, non-antimicrobial therapeutic agents may be incorporated in this coating to treat, prevent, modify, or stimulate certain clinical bioactivities.

41 Claims, No Drawings

MODIFICATION OF MEDICAL PROSTHESES

CROSS-REFERENCE TO RELATED APPLICATIONS

This application claims priority to U.S. provisional application Ser. No. 60/558,918, filed on Apr. 2, 2004.

TECHNICAL FIELD

The present invention relates to indwelling or implanted medical devices treated with a therapeutic agent. Preferably, the implanted medical device is treated with an antimicrobial agent to inhibit the growth of bacterial and fungal organisms. The invention also relates to a method of treating indwelling or implanted medical devices with an antimicrobial agent.

BACKGROUND OF THE INVENTION

Indwelling medical devices such as catheters and orthopedic devices are becoming essential to patient care. The benefit derived from these catheters, orthopedic devices, and other types of medical implants, however, is often offset by infectious complications.

Some of the common organisms causing infectious complications associated with indwelling medical devices are *Staphylococcus epidermidis* and *Staphylococcus aureus*. In the case of vascular catheters, these two organisms account for almost 70–80% of all infectious organisms, with *Staphylococcus epidermidis* being the most common organism. Gram-negative bacilli cause about 15–20% of the infections, and *Candida* species, a fungal agent, accounts for about 10–15% of the vascular catheter infections. Other gram-negative bacteria and fungal organisms (*Candida*) account for the remaining one-third of cases.

Another common hospital-acquired infection is a urinary tract infection (UTI). The majority of UTI cases are associated with the use of urinary catheters, including transurethral foley, suprapubic and nephrostomy catheters. These urinary catheters are inserted in a variety of populations, including the elderly, stroke victims, spinal cord-injured patients, postoperative patients and those with obstructive uropathy. Despite adherence to sterile guidelines for the insertion and maintenance of urinary catheters, catheter-associated UTI continues to pose a major problem. In the U.S. alone, about 1 million cases of hospital-acquired cases of UTI occur annually. For instance, it is estimated that almost one-quarter of hospitalized spinal cord-injured patients develop symptomatic UTI during their hospital course. Gram-negative bacilli account for almost 60–70%, enterococci for about 25% and Canada species for about 10% of cases of UTI.

Colonization of bacteria on the surfaces of the implant or other parts of the device can produce serious patient problems, including the need to remove and/or replace the implanted device and to vigorously treat secondary infective conditions. A considerable amount of attention and study has been directed toward preventing such colonization by the use of antimicrobial agents, such as antibiotics, bound to the surface of the materials employed in such devices. In such attempts, the objective has been to produce a sufficient bacteriostatic or bactericidal action to prevent colonization.

Various methods have previously been employed to prevent infection of medical devices. A simple method is to flush the surfaces of a device with an antimicrobial solution. Generally, this flushing technique requires convenient access to the implantable device. For example, catheters are generally amenable to flushing with a solution of rifampin and minocycline or rifampin and novobiocin. For use in flushing solutions, the effective concentration of the antibiotic range from about 1 to 10 mg/ml for minocycline, preferably about 2 mg/ml; 1 to 10 mg/ml for rifampin, preferably about 2 mg/ml; and 1 to 10 mg/ml for novobiocin, preferably about 2 mg/ml. The flushing solution is normally composed of sterile water or sterile saline solutions.

Other methods of coating surfaces of medical devices with antimicrobial agents are taught in U.S. Pat. No. 4,895,566 (a medical device substrate carrying a negatively charged group having a pKa of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ironically bind antibiotics); U.S. Pat. No. 5,013,306 (laminating an antibiotic to a polymeric surface layer of a medical device); U.S. Pat. No. 4,952,419 (applying a film of silicone oil to the surface of an implant and then contacting the silicone film bearing surface with antibiotic powders); and U.S. Pat. No. 4,442,133.

These and other methods of coating medical devices with antimicrobial agents appear in numerous patents and medical journal articles. However, these methods also have significant drawbacks in that they can alter the integrity of non-metallic medical devices or result in residual antimicrobial material precipitating within the device. In U.S. Pat. No. 6,589,591 and published U.S. Patent Application No. 2003/0229401, Mansouri et al describe a glycerol-based antimicrobial coating for medical implants. Both U.S. Pat. No. 6,589,591 and published U.S. patent application 2003/0229401 are incorporated by reference as though fully set out herein. The coating and resulting medical device provides a broad range of antimicrobial activity while minimizing harmful side effects. However, further improvements involving a slow release mechanism to delay exhaustion of the antimicrobial or other therapeutic agents is still desired.

Accordingly, there is a need for a medical device treated with an antimicrobial agent to provide a broad range of antimicrobial activity while minimizing the harmful side effects noted above. More generally, it would be useful to have medical devices treated with therapeutic agents. Further, there is a need for a method that results in low residual coating material left on the surface of the medical device, which reduces complications arising from precipitation of coating material within the device. There is also a need to enhance the versatility of the treatment to accommodate higher concentrations of antimicrobial agents if needed, and to provide a slow release mechanism to delay exhaustion of the antimicrobial or other therapeutic agents. There is also a need for durable resilient coatings for medical implants to endure possible abrasion or deterioration caused by physical movements or the environment in which the medical device is implanted.

BRIEF SUMMARY OF THE INVENTION

The present invention is directed to a medical implant with a medicated coating and a method of making same.

In one aspect of the invention, there is a method of coating at least a portion of a medical device with a therapeutic agent comprising the steps of: forming a first composition by combining at least the following: a therapeutic agent, an acidic component, a matrix component selected from the group consisting of hide powder, collagen, gelatin, cartilage, tendon, ligament, bone, keratin, fibrin, albumin, globulin, hydroxylapatite, and any combination thereof; and, glycerol; applying the first composition to at least a portion of the medical device to form a first layer; forming a second composition comprising a cyanoacrylate; and, applying the second composition on the first layer to form a second layer. In some embodiments, the method further comprises the step of drying said first layer. In some embodiments, the step of drying is performed in the dark. In some embodiments, the method further comprises the step of drying said second layer. In some embodiments, the method further comprises the steps of drying the first layer and drying the second layer. In some embodiments, the matrix component is a combination of hide powder and collagen, the hide powder is added to achieve a 5% to 50% (w/v) concentration and the collagen is added to achieve a 0.1% to 20% (w/v) concentration in the first solution. In some embodiments, the acidic component is an acid solvent or acidic solution and the acid solvent or acidic solution is combined with the hide powder or collagen at a temperature range of 25° C. to 90° C. and mixed until a clear homogeneous solution is obtained. In some embodiments, the acid solvent or acidic solution is combined with said hide powder or collagen at a temperature range of 25° C. to 90° C. and mixed until a clear homogeneous solution is obtained. In some embodiments, the glycerol is added such that the final concentration of glycerol is between 0.5% and 10%. In some embodiments, the glycerol in said first composition is added after the therapeutic agent, the acidic component, and the matrix component. In some embodiments, the step of applying the first composition to at least a portion of the medical device is selected from the group consisting of immersing the medical device in the composition, spraying the first composition onto the medical device, pouring the first composition over the medical device, blotting the first composition on the medical device, smearing the first composition on the medical device, rolling the medical device in the first composition, brushing the first composition on the medical device, and any combination thereof. In some embodiments, the cyanoacrylate is selected from the group consisting of methyl cyanoacrylate, ethyl cyanoacrylate, butyl cyanoacrylate, octyl cyanoacrylate, hexyl cyanoacrylate, decyl cyanoacrylate, methoxy ethyl cyanoacrylate, isoamyl cyanoacrylate, isopropyl cyanoacrylate and any combination thereof. In some embodiments, the step of applying the second composition is selected from the group consisting of immersing the medical device in the second composition, spraying the second composition onto the medical device, pouring the second composition over the medical device, blotting the second composition on the medical device, smearing the second composition on the medical device, rolling the medical device in the second composition, brushing the second composition on the medical device, and any combination thereof. In some embodiments, the method further comprises drying the first layer from about 1 hour to about 24 hours. In some embodiments wherein the first layer is dried from about 1 hour to about 24 hours, the first layer is dried for about 16 hours. In some embodiments, the method further comprises the step of drying the second layer from about 5 minutes to about 18 hours. In some embodiments wherein the second layer is dried from about 5 minutes to about 18 hours, the second layer is dried for about 12 hours. In some embodiments, the method further comprises the step of applying a cyanoacrylate coat as a primer before the step of applying said first composition. In some embodiments, the method further comprises the step of controlling the viscosity of the second composition comprising a cyanoacrylate. In some embodiments, the method further comprises the step of controlling the temperature of the second composition comprising a cyanoacrylate. In some embodiments, the method further comprises the step of exposing the coating device to moisture after the step of applying the second composition on the first layer. In some embodiments, the first composition comprises hide powder at a concentration of about 29% (w/v). In some embodiments, the first composition comprises collagen at a concentration of about 0.5% (w/v). In some embodiments, the first composition comprises glycerol at a concentration of about 1.25% (w/v). In some embodiments, the therapeutic agent comprises a combination selected from the group consisting of: at least one antibiotic and at least one antiseptic; at least one antibiotic and at least one disinfectant; at least one antiseptic and at least one disinfectant; and, at least one antimicrobial agent. In some embodiments, the therapeutic agent comprises at least one antimicrobial agent.

In another aspect of the present invention, there is an implantable medical device comprising: a body having one or more surfaces; a first coating on at least a portion of the body, the first coating comprising: glycerol, a therapeutic agent, an acidic component, and; a matrix component selected from the group consisting of hide powder, collagen, gelatin, cartilage, tendon, ligament, bone, keratin, fibrin, albumin, globulin, hydroxylapatite, and any combination thereof; a second coating on at least a portion of the first coating, the second coating comprising a cyanoacrylate. In some embodiments, the therapeutic agent is an antimicrobial agent. In some embodiments, the antimicrobial agent is selected from the group consisting of methylisothiazolone, thymol, α-terpineol, cetylpyridinium chloride, chloroxylenol, hexachlorophene, chlorhexidine and other cationic biguanides, methylene chloride, iodine, iodophores, triclosan, taurinamides, nitrofurantoin, methenamine, aldehydes, azylic acid, heavy metals, benzyl peroxide, alcohols, brilliant green, gentian violet, triacetin, salicylic acid, boric acid, carboxylic acids and their salts, erythromycin, nafcillin, cefazolin, imipenem, astreonam, gentamicin, tobramycin, streptomycin, amikacin, neomycin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, doxcycycline, tetracycline, tigecycline, oritavancin, daptomycin, dalbavancin, linezolid, temafloxacin, tosufloxacin, clinafloxacin, sulbactam, clavulanic acid, amphotericin B, fluconazole, miconazole, ravuconazole, posaconazole, clotrimazole, econazole, tioconazole, oxiconazole, bifonazole, isoconazole, fenticonazole, itraconazole, ketoconazole, voriconazole, terbinafine, caspofungin, anidulafungin, micafungin, nystatin, penicillins, cephalosporins, carbepenems, beta-lactams antibiotics, aminoglycosides, macrolides, lincosamides, glycopeptides, tetracylines, chloramphenicol, quinolones, fucidines, sulfonamides, trimethoprims, rifamycins, oxalines, streptogramins, oxazolidinones, lipepeptides, ketolides, polyenes, azoles, echinocandines, and any combination thereof. In some embodiments, the antimicrobial agent comprises heavy metal. In some embodiments wherein the antimicrobial agent comprises heavy metal, the heavy metal is silver. In some embodiments, the antimicrobial agent is a combination of two antimicrobial agents and is selected from the group consisting of chlorhexidine and methylisothiazolone; chlorhexidine and α-terpineol; thymol and chloroxylenol; thymol and methylisothiazolone; chlorhexidine and cetylpyridinium chloride; chlorhexidine and chloroxylenol; chlorhexidine, methylisothiazolone and thymol; methylisothiazolone and α-terpineol; minocycline and rifampin; and chlorhexidine, methylisothiazolone and α-terpineol. In some embodiments, the antimicrobial agent is an antibiotic. In some embodiments, the antibiotic is selected from the group consisting of penicillins, cephalosporins, carbepenems, other beta-lactams antibiotics, aminoglycosides, amphenicols, ansamycins, macrolides, lincosamides, glycopeptides, polypeptides, tetracylines, chloramphenicol, quinolones, fucidins, sulfonamides, sulfones, nitrofurans, diaminopyrimidines, trimethoprims, rifamycins, oxalines, streptogramins, lipopeptides, ketolides, polyenes, azoles, echinocandins, and any combination thereof. In some embodiments, the therapeutic agent is an antimicrobial agent comprised of minocycline and rifampin. In some embodiments, the therapeutic agent is selected from the group consisting of analgesics, anti-inflammatories, antidepressants, antiparasitics, anticancer drugs, anesthetics, antiallergics, anticoagulants, antidiabetics, antihypercholesterolemics, antihyperlipidemics, antineoplastics, calcium regulators, antihypertensives, antihypotensives, antihypothyroids, antihyperthyroids, antileukemics, antimanics, antiprotozoals, antivirals, reverse transcriptase inhibitors, antiamebics, antiarthritics, antirheumatics, antihemorrhagics, cardiotonics, contraceptives, antipsychotics, antispasmodics, antithrombotics, vasodilators, digestive aids, diuretics, enzymes, steroids, growth stimulators, immunosuppressants, immunomodulators, peristalitic stimulators, respiratory stimulators, and any combination thereof. In some embodiments, the material comprising said medical device is selected from the group consisting of metals, metal alloys, carbon, carbon fibers, carbon polymer, ceramic, rubber, plastic, nylon, silicone, silicon, germanium, tin, gallium arsenide, polyurethane, polyethylene, polyvinyl chloride, polytetrafluoroethylene tetraphthalate, polyethylene tetraphthalate, polytetrafluoroethylene, polyglycolic acid, expanded polytetrafluoroethylene, latex, elastomers, polymers, bioabsorbable polymers such as polyglycolic acid, polylactide-coglycolide, and polylactic acid; non-bioabsorbable polymers such as polymethyl methacrylate; latex, gelatin, collagen, albumin, globulin, and any combination thereof. In some embodiments, the medical device is a catheter selected from the group consisting of peripherally insertable central venous catheters, dialysis catheters, long term tunneled central venous catheters, peripheral venous catheters, short-term central venous catheters, arterial catheters, pulmonary artery Swan-Ganz catheters, urinary catheters, long term non-tunneled central venous catheters, peritoneal catheters, and ventricular catheters. In some embodiments, the medical device is selected from the group consisting of long term urinary devices, tissue bonding urinary devices, penile prostheses, vascular grafts, extravascular grafts, urinary stents, vascular catheter ports, wound drain tubes, drug delivery systems, neurotransmitters, epidural catheters, cerebrospinal fluid draining systems, hydrocephalus shunts, pacemaker systems, implantable stimulators, implantable infusion pumps, ventricular bypass assist devices, tissue expanders, implantable pulse generators, maxillofacial implants, mandibular implants, contraceptive tubal occlusion devices, contraceptive intrauterine devices, artificial anal sphincters, artificial urinary sphincters, vascular dilators, extravascular dilators, intravascular stents, extravascular stents, small joint replacements, temporary joint replacements, urinary dilators, heart valves, orthopedic implants, heart assist devices, mammary implants, dental devices, pacemakers, defibrillators, hip prostheses, knee prostheses, spinal prostheses, shoulder prostheses, joint prostheses, fracture fixation devices, external fixation pins, intramedullary nails, screws, plates, rods, and cages. In some embodiments, the cyanoacrylate is selected from the group consisting of methyl cyanoacrylate, ethyl cyanoacrylate, butyl cyanoacrylate, octyl cyanoacrylate, hexyl cyanoacrylate, decyl cyanoacrylate, methoxy ethyl cyanoacrylate, isoamyl cyanoacrylate, isopropyl cyanoacrylate and any combination thereof. In some embodiments, the therapeutic agent comprises a combination selected from the group consisting of: at least one antibiotic and at least one antiseptic; at least one antibiotic and at least one disinfectant; at least one antiseptic and at least one disinfectant; and, at least one antimicrobial agent.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description. It is to be expressly understood, however, that each example provided is illustrative and non-exhaustive is not intended as a definition of the limits of the present invention.

DETAILED DESCRIPTION OF THE INVENTION

It is readily apparent to one skilled in the art that various embodiments and modifications may be made to the invention disclosed in this application without departing from the scope and spirit of the invention.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein, "acidic component" is broadly defined as any component having acidic properties, including, but not limited to, acid solvents and acidic solutions.

The term "antimicrobial agent" as used in the present invention means any single or combination of antiseptics, antibiotics, disinfectants, and antimicrobial peptides. Some examples antimicrobial agents include, but are not limited to, methylisothiazolone, thymol, α-terpineol, cetylpyridinium chloride, chloroxylenol, hexachlorophene, chlorhexidine and other cationic biguanides, methylene chloride, iodine and iodophores, triclosan, taurinamides, nitrofurantoin, methenamine, aldehydes, azylic acid, silver, platinum, other heavy metals, carbon, benzyl peroxide, alcohols, brilliant green, gentian violet, triacetin, salicylic acid, boric acid, carboxylic acids and their salts, erythromycin, nafcillin, cefazolin, imipenem, astreonam, gentamicin, tobramycin, streptomycin, amikacin, neomycin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, doxcycycline, tetracycline, tigecycline, oritavancin, daptomycin, dalbavancin, linezolid, temafloxacin, tosufloxacin, clinafloxacin, sulbactam, clavulanic acid, amphotericin B, fluconazole, miconazole, ravuconazole, posaconazole, clotrimazole, econazole, tioconazole, oxiconazole, bifonazole, isoconazole, fenticonazole, itraconazole, ketoconazole, voriconazole, terbinafine, caspofungin, anidulafungin, micafungin, nystatin, penicillins, cephalosporins, carbepenems, beta-lactams antibiotics, aminoglycosides, macrolides, lincosamides, glycopeptides, tetracylines, chloramphenicol, quinolones, fucidines, sulfonamides, trimethoprims, rifamycins, oxalines, streptogramins, oxazolidinones, lipepeptides, ketolides, polyenes, azoles, and echinocandines. Other examples of antibiotics, such as those listed in Sakamoto et al, U.S. Pat. No. 4,642,104 herein incorporated by reference will readily suggest themselves to those of ordinary skill in the art. The term "antimicrobial agent" encompasses a single entity or chemical compound as well as more than one entity or chemical compound. Thus, the term "antimicrobial agent" encompasses both the singular and the plural and means one or more than one antimicrobial agent. One of ordinary skill in the art will recognize other possible candidates.

The term "bacterial and fungal organisms" as used in the present invention means all genera and species of bacteria and fungi, including but not limited to all spherical, rod-shaped and spiral organisms. One skilled in the art recognizes that a variety of source books which list and describe bacteria and fungi are available, for example in the textbook "Principles and Practice of Infectious Diseases", Mandell et al., 6$^{th}$ edition, 2004, Churchill Livingstone, N.Y. (also see the 5$^{th}$ edition of the same textbook, published in 2000). Some examples of bacteria are staphylococci (i.e. *Staphylococcus epidermidis, Staphylococcus aureus*), *Enterococcus faecalis, Pseudomonas aeruginosa, Escherichia coli*, other gram-positive bacteria and gram-negative bacilli. One example of a fungus is *Candida albicans*.

The term "glycerol" means 1,2,3-propanetriol, and is also known as glycerin. "Glycerol", "glycerin", and "1,2,3-propanetriol" are used interchangeably herein.

As used herein, the term "heavy metal" is defined as any metallic element that has a relatively high density and is toxic, highly toxic or poisonous at low concentrations. Examples of heavy metals include, but are not limited to, mercury, cadmium, arsenic, chromium, thallium, silver, platinum, and lead.

As used herein, "implanted" devices includes both temporary and permanent devices and indwelling and implanted devices.

As used herein, "cyanoacrylate" refers to cyanoacrylate compounds as they are commonly known in the art. These include, but are not limited to, methyl cyanoacrylate, ethyl cyanoacrylate, butyl cyanoacrylate, octyl cyanoacrylate (including any one or more of N-octyl-cyanoacrylate, 2-octyl cyanoacrylate, iso-octyl cyanoacrylate), hexyl cyanoacrylate, decyl cyanoacrylate, methoxy ethyl cyanoacrylate, isoamyl cyanoacrylate, and isopropyl cyanoacrylate. The term "cyanoacrylate" encompasses a pure cyanocraylate, a mixture of pure cyanoacrylates, or a solution of one or more cyanoacrylates. One of ordinary skill in the art will recognize other possible candidates.

As used herein, the term "therapeutic agent" is given its broadest definition as known by one of ordinary skill in the art. "Therapeutic agent" therefore encompasses any agent that treats or prevents a disease or pathological condition or otherwise promotes health, including, but not limited to, drug substances, antimicrobial agents, antiseptics, antibiotics, disinfectants, and antimicrobial peptides, genetic materials including any nucleic acids, nucleotides, nucleosides, proteins, etc. The term "therapeutic agent" encompasses the singular and the plural, and thus means both one therapeutic agent or more than one therapeutic agent.

As used herein, "tivanium" is an alloy of titanium, aluminum, and vanadium, having the composition Ti6Al4V.

Any therapeutic agent, or combinations thereof, may be used in the present invention. Some examples include, but are not limited to, analgesics, anti-inflammatories, antidepressants, antiparasitics, antimicrobials, anticancer drugs, anesthetics, antiallergics, anticoagulants, antidiabetics, antihypercholesterolemics, antihyperlipidemics, antineoplastics, calcium regulators, antihypertensives, antihypotensives, antihypothyroids, antihyperthyroids, antileukemics, antimanics, antiprotozoals, antivirals, reverse transcriptase inhibitors, antiamebics, antiarthritics, antirheumatics, antihemorrhagics, cardiotonics, contraceptives, antipsychotics, antispasmodics, antithrombotics, vasodilators (including cerebral, coronary, and other vasodilators), digestive aids, diuretics, enzymes, steroids, growth stimulators, immunosuppressants, immunomodulators, peristalitic stimulators, and respiratory stimulators, Any combination thereof may also be used. One of ordinary skill in the art will recognize other possible candidates.

Combinations of therapeutic agents may be used for their synergistic effect. Some preferred examples include combinations comprising at least one antibiotic and at least one antiseptic; combinations comprising at least one antibiotic and at least one disinfectant; combination comprising at least one antiseptic and at least one disinfectant; and, combinations comprising at least one antimicrobial agent. These are non-limiting examples provided by way of illustration. Others combinations are possible and will be apparent to one of ordinary skill in the art upon reading this disclosure.

When antimicrobial agents are used, they are preferably used in combinations of two or more to obtain a synergistic effect. They are dispersed along the surface of the medical device to provide a broad range of antimicrobial activity. Some examples include, but are not limited to, chlorhexidine and methylisothiazolone; chlorhexidine and α-terpineol; thymol and chloroxylenol; thymol and methylisothiazolone; chlorhexidine and cetylpyridinium chloride; chlorhexidine and chloroxylenol; chlorhexidine, methylisothiazolone and thymol; methylisothiazolone and α-terpineol; minocycline and rifampin; and chlorhexidine, methylisothiazolone and α-terpineol. These combinations provide a broad spectrum of activity against a wide variety of organisms. One of ordinary skill in the art will recognize other possible candidates.

The amount of antimicrobial agent used to treat a medical device varies to some extent, but is at least a sufficient amount to form an effective concentration to inhibit the growth of bacterial and fungal organisms, such as staphylococci, gram-positive bacteria, gram-negative bacilli and *Candida*.

The term "effective concentration" means a sufficient amount of an antimicrobial agent to decrease, prevent or inhibit the growth of bacterial and/or fungal organisms. The amount will vary for each compound and upon known factors such as pharmaceutical characteristics; the type of medical device; age, sex, health and weight of the recipient, and the use and length of use. It is within the skilled artisan's ability to relatively easily determine an effective concentration of an antimicrobial agent for different antimicrobial agents and different known factors.

The antimicrobial agents may be antiseptics. The use of antiseptics may provide more efficacy against gram-negative bacteria and *Candida* species than antibiotic combinations. Although the different mixtures of antiseptics can be used for all medical devices, certain mixtures work better with different devices. Different combinations of antiseptics can be used for different types of medical devices depending on the spectrum of organisms that cause the infections related to each device. For instance, preferred combinations of treating orthopedic devices include chlorhexidine, methylisothiazolone and α-terpineol; chlorhexidine and cetylpyridinium chloride; chlorhexidine and chloroxylenol; or chlorhexidine, methylisothiazolone and thymol. The combination of different antiseptics has a synergistic effect against certain bacteria and fungi. One of ordinary skill in the art will recognize other possible candidates.

The antimicrobial agents may be antibiotics. Some examples include, but are not limited to, penicillins, cephalosporins, carbepenems, other beta-lactams antibiotics, aminoglycosides, amphenicols, ansamycins, macrolides, lincosamides, glycopeptides, polypeptides, tetracylines, chloramphenicol, quinolones, fucidins, sulfonamides, sulfones, nitrofurans, diaminopyrimidines, trimethoprims, rifamycins, oxalines, streptogramins, lipopeptides, ketolides, polyenes, azoles, echinocandins; any combination thereof is also possible. One of ordinary skill in the art will be familiar with other potential candidates upon a reading of the list of examples provided above.

The medical devices which are amenable to treatment according to one aspect of the present invention may be metallic or non-metallic. Additionally, the metallic or non-metallic portion, or both, of devices having both metallic and non-metallic portions may be treated. Treatable medical devices may also include devices that are formed from more than one type of non-metallic or metallic material.

Non-metallic materials that can be treated by the method of the present invention include, but are not limited to, rubber, plastic, ceramic, nylon, silicone, silicon, germanium, tin, gallium arsenide, polyurethane, polyethylene, polyvinyl chloride, carbon, carbon fibers, carbon polymer, Gortex (polytetrafluoroethylene tetraphthalate), Dacron (polyethylene tetraphthalate), Teflon (polytetrafluoroethylene or PTFE), expanded polytetrafluoroethylene (ePTFE), latex, elastomers, polymers, bioabsorbable polymers (including, but not limited to, polyglycolic acid (PGA), polylactide-co-glycolide, and polylactic acid (PLA) and non-bioabsorbable polymers (e.g., polymethyl methacrylate), gelatin, collagen, globulin, or albumin. Any combination thereof is also possible. One of ordinary skill in the art will recognize other possible candidates.

Metallic devices treatable by the method of the present invention include, but are not limited to, all of the conventional metals and metal alloys commonly used in medical implants, including, but not limited to, cobalt-chromium, titanium, stainless steel, tivanium, gold, silver, zirconium, hafnium, and others, including any alloys thereof. In addition, any non-conventional metals or metal alloys are also treatable by the method of the present invention.

Particular medical devices suited for the modification with therapeutic agents according to the present invention include, but are not limited to, peripherally insertable central venous catheters, dialysis catheters, long term tunneled central venous catheters, long term non-tunneled central venous catheters, peripheral venous catheters, short-term central venous catheters, arterial catheters, pulmonary arty Swan-Ganz catheters, urinary catheters, long term urinary devices, tissue bonding urinary devices, penile prostheses, vascular grafts, extravascular grafts, urinary stents, vascular catheter ports, wound drain tubes, drug-delivery systems, neurotransmitters, epidural catheters, cerebrospinal fluid draining systems, hydrocephalus shunts, peritoneal catheters, pacemaker systems, implantable stimulators (examples of which include, but are not limited to, cerebellar stimulators, nerve stimulators, intracerebral/subcortical stimulators, spinal cord stimulators, neuromuscular stimulators, peripheral nerve stimulators), implantable infusion pumps, ventricular bypass assist devices, tissue expanders, implantable pulse generators, maxillofacial implants, mandibular implants, contraceptive tubal occlusion devices, contraceptive intrauterine devices, artificial anal sphincters, artificial urinary sphincters, vascular dilators, extravascular dilators, intravascular stents, extravascular stents, ventricular catheters, small joint replacements, temporary joint replacements, urinary dilators, heart valves, orthopedic implants, heart assist devices, mammary implants, dental devices, pacemakers, defibrillators, joint prostheses, fracture fixation devices, external fixation pins, intramedullary nails, screws, plates, rods, cages, and the like. Drug delivery systems include all such systems used for, inter alia, intravascular, extravascular, cardiovascular, epidermal, epidural, paraspinal, spinal, ventricular, intra-arterial, intramuscular, intravenous, musculoskeletal, intrapelvic, intrapulmonary, intracranial, intraperitoneal, intraabdominal, intracephalic, and genitourinary drug deliveries.

With respect to the modification of medical device with antimicrobial agents, the present invention may also be used to treat miscellaneous surfaces, such as hospital floors, nursing counters, counters adjacent to washing basins, desks, etc. to decrease transmission of hospital antibiotic-resistant microbial flora, such as methicillin-resistant *Staphylococcus aureus*, vancomycin-resistant *Enterococci* and antibiotic-resistant gram negative bacteria on the skin of health care personnel and patients. Another potential application is the treatment of kitchen counters to decrease transmission of organisms that cause food-borne poisoning, such as *Salmonella* species and *Escherichia coli*.

The medical device may be treated with a therapeutic composition by applying a sufficient amount of the therapeutic composition to at least a portion of the medical device under conditions wherein at least a portion of the therapeutic composition binds with the medical device. Although it is contemplated that the antimicrobial agents will bind with the medical device, other ingredients such as anti-coagulants and anti-inflammatory agents may be included in the therapeutic composition and may also bind and or promote binding of the therapeutic agent with the medical device.

Broadly, the method of making the medical device of the present invention comprises the following steps. A first composition is formed by combining at least the following: a therapeutic agent; an acidic component; glycerol; and a matrix component selected from the group consisting of hide powder, collagen, gelatin, cartilage, tendon, ligament, bone, keratin, fibrin, albumin, globulin, hydroxylapatite (also known in the literature as "hydroxyapatite"), and any combination thereof. The matrix component is a biocompatible material which act as the medium which holds the other components of the first composition. The first composition is applied to at least a portion of the medical device to form a first layer. A second composition is formed; the second composition comprises a cyanoacrylate. The second composition is applied on the first layer to form a second layer. The resulting improved medical device can be used, for example, to prevent, treat, or reduce bacterial and fungal infections associated with these implants. Additionally, the therapeutic agents can be used to effect other therapeutic benefits.

The following examples are not exhaustive and offered by way of illustration and are not intended to limit the invention in any manner. Although the examples are limited to the use of antimicrobials to modify medical devices, it should be understood by those of ordinary skill in the art that therapeutic agents generally may be used to modify medical devices according to the present invention.

Methods and Materials

This method is a bilayer technique applied in two steps. The first layer, applied in the first step, consists of a solution of hide powder (preferably from 5% (w/v) to 50% (w/v); most preferably at about 29% (w/v)) or collagen (preferably from 0.1% (w/v) to 20% (w/v); most preferably at about 0.5% (w/v)) or a combination of both, and preferably an acid solvent or acidic solution (the latter may include mixtures of acids) of a weak acid, non-limiting examples of which include a saturated short chain monocarboxylic acid such as acetic, formic, or propionic acid with a liquidity state below 90° C. and above 110° C. and a pKa of 3 to 5. However, other solvents may also be used, including various alcohols and other, preferably protic solvents. Water, preferably deionized distilled water, may be added to reduce the acidity to the desired pH. This solvent is added to the collagen or hide powder at room temperature or elevated temperature (preferably between 25° C. to 90° C.) until a homogeneous clear solution is observed. In parallel, a solution of antimicrobial agent is prepared in the same solvent at a temperature compatible with the antimicrobial agent. Using the combination of minocycline and rifampin as an example of antimicrobial agents, these antibiotics are added at the concentrations of up to 300 mg per ml of the total volume of the solution. The order of addition of these antibiotics is not critical and may be varied, however, it is easier to monitor dissolution of minocycline fully before adding rifampin than vice versa. Once the hide powder and/or collagen is dissolved completely, the antimicrobial solution is added to the solution at room temperature. If using collagen in the first layer, the antimicrobial agents may be added to the collagen solution rather than a separate solvent. The final component of the solution is glycerol (also called glycerin or 1,2,3-propanetriol) at preferably between about 0.5% (v/v) and 10% (v/v) (most preferably at about 1.25% (v/v)). Glycerol is preferably added last to avoid difficulties in dissolving collagen/hide powder and antibiotics at a higher viscosity that glycerin adds to the coating solution. Glycerol acts as a plasticizer and lubricant to prevent the collagen or hide solution from becoming brittle. It also enhances the amalgamation of the coating solution with the antimicrobial agents during the coating process. The collagen used in the present invention may be synthetic or natural (either from human or non-human sources). Hide powder is commercially available and known to those skilled in the art and comprises denatured collagen.

The so prepared solution may be applied to the medical device by immersing the device in the solution, spraying the solution on the device, or pouring the solution over the device. In one example, the device is completely submerged into the solution for a period of time that can vary depending on the nature of the device to be coated. This period is preferably 1 minute (the preferred range is between 1 second to 2 hours) and may be increased to assure the binding of the coating layer, or reduced to preserve the integrity of the implant material. Any other suitable method, known to those of ordinary skill in that art, of applying a composition to a surface may also be used. After the first coating layer is applied, the device is placed under a well-ventilated fume hood between 1 and 24 hours (preferably about 16 hours). Preferably, the drying processes are performed in a well-ventilated, dark fume hood to avoid any side reactions initiated by light (e.g., free radical reactions). The second coating is preferably applied after the first coating layer has dried.

In the second step, a protective layer is applied on top of the first antimicrobial-containing layer. This second layer is a safe, waterproof, durable fast-drying layer, which may control the release of antimicrobial agents over an extended period of time while delaying the exhaustion of the reservoir of antimicrobial agents. This layer is formed by applying, on the first layer, a composition comprising a cyanoacrylate, which may include one or more of methyl cyanoacrylate, ethyl cyanoacrylate, butyl cyanoacrylate, octyl cyanoacrylate (including any one or more of N-octyl-cyanoacrylate, 2-octyl cyanoacrylate, iso-octyl cyanoacrylate) hexyl cyanoacrylate, decyl cyanoacrylate, methoxy ethyl cyanoacrylate, isoamyl cyanoacrylate, or isopropyl cyanoacrylate. Cyanoacrylates create a high quality tenacious polymeric layer. The cyanoacrylate composition is preferably in liquid form and may be one or more pure cyanoacrylates in liquid form, or it can be one or more cynoacrylates dissolved in a suitable solvent. The second layer is applied under a well-ventilated fume hood by immersing the medical device in the solution, spraying the solution onto the device, or pouring the solution over the device. In one example, the device is completely submerged into the solution for a period of 5 seconds (range from 1 second to 60 seconds depending on the device). After the second coating layer is applied, the device is placed under a well-ventilated (preferably dark) fume hood for preferably about 12 hours for drying (drying time may vary from 5 minutes to 18 hours). The lower the viscosity of cyanoacrylate, the quicker the second layer will polymerize and dry. One may also use cyanoacrylate compositions of different viscosities to control the thickness of the layer deposited; a more viscous cyanoacrylate will more easily afford thicker coating layers. In addition, drying time increases with elongation of the side chain (e.g. methyl, ethyl, butyl, octyl). Also, changing the temperature of the cyanoacrylate, within its liquidity and within a range undisruptive to the device as well as all the coating agents and antimicrobial agents, may be used to modify its viscosity and in turn to control the thickness of the coated layer. The higher the temperature, the lower the viscosity of cyanoacrylate will be. Consequently, the lower the viscosity, the thinner the thickness of the coated layer will be. The lower the viscosity, the quicker the second layer will polymerize and dry. Other viscosity modification techniques, known to those skilled in the art, are applicable. To reduce the setting time (drying time) for longer chain cyanoacrylates, they may be mixed with smaller chain cyanoacrylates when appropriate. Small amounts of antimicrobial agents may be dissolved in cyanoacrylate prior to applying the second coating layer to provide a primary reservoir of antimicrobial agents. After the second layer is applied, the coated device may be exposed to moisture (e.g. water vapor or traces of sprayed water) to help catalyze/speed up the polymerization of cyanoacrylate. Furthermore, a cyanoacrylate coat may be applied prior to the first layer as a primer to hold the collagen/hide layer stronger if needed.

This method produces very low floating residual material on the surface of the medical device with a glossy uniform coating. It also enhances the versatility of the solution to accommodate higher concentrations of coating agents if needed. In addition, an acidic environment is more desirable and easier to dissolve a variety of drug and coating agents. The first coating layer is composed of a natural compound, collagen, hide powder, gelatin (also called gelatine), cartilage, tendon, ligament, bone, keratin, or fibrin, which is clinically biocompatible. In addition, glycerin is a safe compound that has been used in medicine and food and in the cosmetic industries. The second layer consists of a cyanaoacrylate. Cyanoacrylates have been used in medicine for decades. Some medical uses of these compounds include embolization of cerebral arteiovenous malformation, periodontal therapy, skin closure agents, management of cerebrospinal fluid leakage, treatment of facial bone fractures, treatment of symptomatic nephroptosis, treatment of erective impotence, and treatment of corneal perforations.

The antimicrobial bilayer may be applied to medical devices made of any material. Such material may include, as non-limiting examples, metals (e.g., stainless steel, titanium, tivanium, gold, silver, and others), metal alloys, ceramic, rubber, plastic, nylon, silicone, polyurethane, polyethylene, polyvinyl chloride, polytetrafluoroethylene tetraphthalate, polyethylene tetraphthalate, polytetrafluoroethylene (PTFE), expanded polytetrafluoroethylene (ePTFE), latex, bioabsorbable polymers (including, but not limited to, polyglycolic acid (PGA), polylactide-co-glycolide, polylactic acid (PLA), and others), non-bioabsorbable polymers (e.g., polymethyl methacrylate and others), gelatin, collagen, albumin and any combination thereof. The medical device itself may be any indwelling device. Non-limiting examples include catheters including catheter peripherally insertable central venous catheters, dialysis catheters, long term tunneled central venous catheters, peripheral venous catheters, short-term central venous catheters, arterial catheters, pulmonary artery Swan-Ganz catheters, urinary catheters, long term non-tunneled central venous catheters, peritoneal catheters, and ventricular catheters. Additional non-limiting examples include urinary devices, tissue bonding urinary devices, penile prostheses, vascular grafts, extravascular grafts, urinary stents, vascular catheter ports, wound drain tubes, drug-delivery systems, neurotransmitters, epidural catheters, cerebrospinal fluid draining systems, hydrocephalus shunts, pacemaker systems, implantable stimulators (examples of which include, but not limited to, cerebellar stimulators, nerve stimulators, intracerebral/subcortical stimulators, spinal cord stimulators, neuromuscular stimulators, peripheral nerve stimulators), implantable infusion pumps, ventricular bypass assist devices, tissue expanders, implantable pulse generators, maxillofacial implants, mandibular implants, contraceptive tubal occlusion devices, contraceptive intrauterine devices, artificial anal sphincters, artificial urinary sphincters, vascular dilators, extravascular dilators, intravascular stents, extravascular stents, small joint replacements, temporary joint replacements, urinary dilators, heart valves, orthopedic implants, heart assist devices, mammary implants, dental devices, pacemakers, and defibrillators. Also, the device may be a conventional orthopaedic implant such as hip prostheses, knee prostheses, spinal prostheses, shoulder prostheses, other joint prostheses, fracture fixation devices, external fixation pins, intramedullary nails, screws, plates, rods, cages and any other prostheses.

The following are provided as non-limiting examples of specific embodiments of the present invention. It should be understood that the present invention is not limited to these examples and that one of ordinary skill in the art will recognize that various changes may be made without departing from the scope of the present invention.

Results and Data

EXAMPLE 1

Titanium-Hide-M/R-ECA

Titanium cylinders, which were made from the same material used in a variety of orthopedic devices, were used for treatment. A solution of 17.5 ml of glacial acetic acid (also called ethanoic acid or methane carboxylic acid, having a pKa of 4.74) with 5 g of non-chromated hide powder (about 29% (w/v)) from bovine skin was prepared at 80° C. and brought to room temperature. Another solution was prepared at room temperature by dissolving 2 g of minocycline and 2 g of rifampin in 17.5 ml of glacial acetic acid. The two solutions were then mixed at room temperature and 0.5 ml of glycerol (glycerin) was added to the final solution as a plasticizer. Titanium cylinders were immersed in the final solution for 30 seconds and then placed under a dark well-ventilated fume hood over night. The second layer was applied under a well-ventilated fume hood by immersing the devices in a solution of ethyl cyanoacrylate for 5 seconds. After the second coating layer was applied the devices were placed under a dark well-ventilated fume hood for about 12 hours for drying.

Upon drying, the antimicrobial activity of the coated devices were measured by performing a modified Kirby-Bauer method. Five devices were set aside for baseline antimicrobial activity. Another ten devices were placed in serum at 37° C. Samples were removed after 7 days and 14 days. Zones of inhibition were performed for baseline, day 7, and day 14 against Staphylococcus epidermidis, Staphylococcos aureus, Pseudomonas aeruginosa, Escherichia coli, and Candida albicans according to Kirby-Bayer method. Each device was half embedded in the center of a Muller-Hinton agar plate that had been previously inoculated with individual organisms. Prior to placing the segments in agar, each organism was grown for 18 hours in trypticase soy broth to a concentration of 0.5 McFarland U ($10^8$ cfu/ml). A cotton swab was placed in the suspension and streaked across the surface of the Muller-Hinton agar plate to cover the entire plate. All plates were placed in the 37° C. incubator for at least 24 hours. The external diameter of the titanium devices was ca. 12 mm. Zones of inhibition were measured the next day and shown in Table 1.

TABLE 1

Zones of Inhibition with Minocycline/Rifampin Coated Titanium Cylinders (mm).

| | Staphylococcus epidermidis | Staphylococcus aureus | Pseudomonas aeruginosa | Escherichia coli | Candida albicans |
|---|---|---|---|---|---|
| Baseline | 51 | 39 | 16 | 32 | 21 |
| Day 7 | 56 | 37 | 29 | 35 | 28 |
| Day 14 | 51 | 40 | 24 | 32 | 22 |

EXAMPLE 2

Stainless Steel-Hide-M/R-OCA

One-centimeter segments of stainless steel fixation pins were used for treatment. A solution of 17.5 ml of glacial acetic acid with 5 g of non-chromated hide powder (about 29% (w/v)) from bovine skin was prepared at 80° C. and brought to room temperature. Another solution was prepared at room temperature by dissolving 2 g of minocycline and 2 g of rifampin in 17.5 ml of glacial acetic acid. The two solutions were then mixed at room temperature and 0.5 ml of glycerol (glycerin) was added to the final solution as a plasticizer. The segments were immersed in the final solution for 30 seconds and then placed under a dark well-ventilated fume hood over night. The second layer was applied under a well-ventilated fume hood by immersing the medical devices in a solution of 2-octyl cyanoacrylate for 5 seconds. After the coating layer was applied, the devices were placed under a dark well-ventilated fume hood for about 12 hours for drying.

Upon drying, the antimicrobial activity of the coated devices were measured by performing a modified Kirby-Bauer method. Five segments were set aside for baseline antimicrobial activity. Another five segments were placed in serum at 37° C. Samples were removed after 7 days. Zones of inhibition were performed against *Staphylococcus epidermidis*, *Staphylococcus aureus*, *Pseudomonas aeruginosa*, *Escherichia coli*, and *Candida albicans* according to Kirby-Bauer method. Each device was half embedded in the center of a Muller-Hinton agar plate that had been previously inoculated with individual organisms. Prior to placing the segments in agar, each organism was grown for 18 hours in trypticase soy broth to a concentration of 0.5 McFarland U ($10^8$ cfu/ml). A cotton swab was placed in the suspension and streaked across the surface of the Muller-Hinton agar plate to cover the entire plate. All plates were placed in a 37° C. incubator for at least 24 hours. The external diameter of the titanium devices was ca. 3 mm. Zones of inhibition were measured and are shown in Table 2.

TABLE 2

Zones of Inhibition with Minocycline/Rifampin Coated Fixation Pin Segments (mm).

| | Staphylococcus epidermidis | Staphylococcus aureus | Pseudomonas aeruginosa | Escherichia coli | Candida albicans |
|---|---|---|---|---|---|
| Baseline | 50 | 31 | 29 | 29 | 23 |
| Day 7 | 49 | 25 | 21 | 25 | 15 |

EXAMPLE 3

Titanium-Collagen-M/R-ECA

Titanium cylinders, which were made from the same material used in a variety of orthopedic devices, were used for treatment. A solution of 10 ml of glacial acetic acid with 500 mg of minocycline and 500 mg of rifampin was prepared at room temperature. 50 mg of acid soluble collagen from New Zealand White rabbit skin (about 0.5% (w/v)) and 120 μl of glycerol were added to this solution at room temperature. The devices were immersed in this solution for 30 seconds and then placed under a dark well-ventilated fume hood over night. The second layer was applied under a well-ventilated fume hood by immersing the devices in a solution of ethyl cyanoacrylate for 5 seconds. After the second coating layer was applied, the devices were placed under a dark well-ventilated fume hood for about 12 hours for drying.

Upon drying, the antimicrobial activity of the coated devices were measured by performing a modified Kirby-Bauer method. Five devices were used for baseline antimicrobial activity. Zones of inhibition were performed against *Staphylococcus epidermidis*, *Staphylococcus aureus*, *Pseudomonas aeruginosa*, *Escherichia coli*, and *Candida albicans* according to Kirby-Bauer method. Each device was half embedded in the center of a Muller-Hinton agar plate that had been previously inoculated with individual organisms. Prior to placing the segments in agar, each organism was grown for 18 hours in trypticase soy broth to a concentration of 0.5 McFarland U ($10^8$ cfu/ml). A cotton swab was placed in the suspension and streaked across the surface of the Muller-Hinton agar plate to cover the entire plate. All plates were placed in a 37° C. incubator for at least 24 hours. The external diameter of the titanium devices was ca. 12 mm. Zones of inhibition were measured and are shown in Table 3.

TABLE 3

Zones of Inhibition with Minocycline/Rifampin Coated Titanium Cylinders (mm).

| | Staphylococcus epidermidis | Staphylococcus aureus | Pseudomonas aeruginosa | Escherichia coli | Candida albicans |
|---|---|---|---|---|---|
| Baseline | 41 | 18 | 15 | 18 | 15 |

EXAMPLE 4

Stainless Steel-Collagen-M/R-OCA

One-centimeter segments of stainless steel fixation pins were used for treatment. A solution of 10 ml of glacial acetic acid with 500 mg of minocycline and 500 mg of rifampin was prepared at room temperature. 50 mg of acid soluble collagen from New Zealand White rabbit skin (about 0.5% (w/v)) and 120 μl of glycerol were added to this solution at room temperature. The segments were immersed in this solution for 30 seconds and then placed under a dark well-ventilated fume hood over night. The second layer was applied under a well-ventilated fume hood by immersing the devices in a solution of 2-octyl cyanoacrylate for 5 seconds. After the second coating layer was applied, the devices were placed under a dark well-ventilated fume hood for about 12 hours of drying.

Upon drying, the antimicrobial activity of the coated devices were measured by performing a modified Kirby-Bauer method. Five devices were used for baseline antimicrobial activity. Zones of inhibition were performed against *Staphylococcus epidermidis*, *Staphylococcus aureus*, *Pseudomonas aeruginosa*, *Escherichia coli*, and *Candida albicans* according to Kirby-Bauer method. Each device was half embedded in the center of a Muller-Hinton agar plate that had been previously inoculated with individual organisms. Prior to placing the segments in agar, each organism was grown for 18 hours in trypticase soy broth to a concentration of 0.5 McFarland U ($10^8$ cfu/ml). A cotton swab was placed in the suspension and streaked across the surface of the Muller-Hinton agar plate to cover the entire plate. All plates were placed in a 37° C. incubator for at least 24 hours. The external diameter of the titanium devices was ca. 3 mm. Zones of inhibition were measured and are provided in Table 4.

TABLE 4

Zones of Inhibition with Minocycline/Rifampin Coated Fixation Pin Segments (mm).

| | Staphylococcus epidermidis | Staphylococcus aureus | Pseudomonas aeruginosa | Escherichia coli | Candida albicans |
|---|---|---|---|---|---|
| Baseline | 44 | 23 | 14 | 25 | 16 |

EXAMPLE 5

Titanium-Collagen-CH/CX-ECA

Titanium cylinders, which were made from the same material used in a variety of orthopedic devices, were used for treatment. A solution of 10 ml of glacial acetic acid with 500 mg of chlorhexidine and 250 mg of chloroxylenol was prepared at room temperature. 50 mg of acid soluble collagen from New Zealand White rabbit skin (about 0.5% (w/v)) and 120 µl of glycerol were added to this solution at room temperature. The devices were immersed in this solution for 30 seconds and then placed under a dark well-ventilated fume hood over night. The second layer was applied under a well-ventilated fume hood by immersing the devices in a solution of ethyl cyanoacrylate for 5 seconds. After the second coating layer was applied, the devices were placed under a dark well-ventilated fume hood for about 12 hours of drying.

Upon drying, the antimicrobial activity of the coated devices were measured by performing a modified Kirby-Bauer method. Five devices were used for baseline antimicrobial activity. Zones of inhibition were performed against *Staphylococcus epidermidis, Staphylococcus aureus, Pseudomonas aeruginosa, Escherichia coli*, and *Candida albicans* according to Kirby-Bauer method. Each device was half embedded in the center of a Muller-Hinton agar plate that had been previously inoculated with individual organisms. Prior to placing the segments in agar, each organism was grown for 18 hours in trypticase soy broth to a concentration of 0.5 McFarland U ($10^8$ cfu/ml). A cotton swab was placed in the suspension and streaked across the surface of the Muller-Hinton agar plate to cover the entire plate. All plates were placed in a 37° C. incubator for at least 24 hours. The external diameter of the titanium devices was ca. 12 mm. Zones of inhibition were measured the next day and are provided in Table 5.

TABLE 5

Zones of Inhibition with Chlorhexidine/Chloroxylenol Coated Titanium Cylinders (mm)

| | Staphylococcus epidermidis | Staphylococcus aureus | Pseudomonas aeruginosa | Escherichia coli | Candida albicans |
|---|---|---|---|---|---|
| Baseline | 43 | 20 | 15 | 16 | 18 |

EXAMPLE 6

Stainless Steel-Collagen—CH/CX-OCA

One-centimeter segments of stainless steel fixation pins were used for treatment. A solution of 10 ml of glacial acetic acid with 500 mg of chlorohexidine and 250 mg of chloroxylenol was prepared at room temperature. 50 mg of acid soluble collagen from New Zealand White rabbit skin (about 0.5% (w/v)) and 120 µl of glycerol were added to this solution at room temperature. The segments were immersed in this solution for 30 seconds and then placed under a dark well-ventilated fume hood over night. The second layer was applied under a well-ventilated fume hood by immersing the devices in a solution of 2-octyl cyanoacrylate for 5 seconds. After the second coating layer was applied, the devices were placed under a dark well-ventilated fume hood for about 12 hours of drying.

Upon drying, the antimicrobial activity of the coated devices were measured by performing a modified Kirby-Bauer method. Five devices were used for baseline antimicrobial activity. Zones of inhibition were performed against *Staphylococcus epidermidis, Staphylococcus aureus, Pseudomonas aeruginosa, Escherichia coli*, and *Candida albicans* according to Kirby-Bauer method. Each device was half embedded in the center of a Muller-Hinton agar plate that had been previously inoculated with individual organisms. Prior to placing the segments in agar, each organism was grown for 18 hours in trypticase soy broth to a concentration of 0.5 McFarland U ($10^8$ cfu/ml). A cotton swab was placed in the suspension and streaked across the surface of the Muller-Hinton agar plate to cover the entire plate. All plates were placed in a 37° C. incubator for at least 24 hours. The external diameter of the titanium devices was ca. 3 mm. Zones of inhibition were measured the next day and are provided in Table 6.

TABLE 6

Zones of Inhibition with Minocycline/Rifampin Coated Fixation Pin Segments (mm)

| | Staphylococcus epidermidis | Staphylococcus aureus | Pseudomonas aeruginosa | Escherichia coli | Candida albicans |
|---|---|---|---|---|---|
| Baseline | 42 | 20 | 12 | 16 | 17 |

EXAMPLE 7

Polyethylene-Collagen-M/R-OCA

In this example, 10 cm polyethylene biliary stents were used for treatment. A solution of 10 ml of glacial acetic acid with 500 mg of minocycline and 500 mg of rifampin was prepared at room temperature. 50 mg of collagen acid soluble collagen from New Zealand White rabbit skin (about 0.5% (w/v)) and 120 µl of glycerol were added to this solution at room temperature. The devices were immersed in this solution for 30 seconds and then placed under a dark well-ventilated fume hood for 5 hours. The second layer was applied under a well-ventilated fume hood by immersing the devices in a solution of 2-octyl cyanoacrylate for 5 seconds.

After the second coating layer was applied, the devices were placed under a dark well-ventilated fume food for about 12 hours of drying.

Upon drying, the antimicrobial activity of the coated devices were measured by performing a modified Kirby-Bauer method. Devices were cut in one-centimeter segments. Five segments were used for baseline antimicrobial activity. Zones of inhibition were performed against *Staphylococcus epidermidis, Staphylococcus aureus, Pseudomonas aeruginosa, Escherichia coli, Candida albicans,* and *Enterococcus faecalis* according to Kirby-Bauer method. Each coated device segment was half embedded in the center of a Muller-Hinton agar plate that had been previously inoculated with individual organisms. Prior to placing the segments in agar, each organism was grown for 18 hours in trypticase soy broth to a concentration of 0.5 McFarland U ($10^8$ cfu/ml). A cotton swab was placed in the suspension and streaked across the surface of the Muller-Hinton agar plate to cover the entire plate. All plates were placed in a 37° C. incubator for at least 24 hours. The external diameter of the biliary stent segments was ca. 3 mm. Zones of inhibition were measured the next day and are provided in Table 7.

Upon drying, the antimicrobial activity of the coated devices were measured by performing a modified Kirby-Bauer method. Devices were cut in one-centimeter segments. Five segments were used for baseline antimicrobial activity. Zones of inhibition were performed against *Staphylococcus epidermidis, Staphylococcus aureus, Pseudomonas aeruginosa, Escherichia coli, Candida albicans,* and *Enterococcus faecalis* according to Kirby-Bauer method. Each coated device segment was half embedded in the center of a Muller-Hinton agar plate that had been previously inoculated with individual organisms. Prior to placing the segments in agar, each organism was grown for 18 hours in trypticase soy broth to a concentration of 0.5 McFarland U ($10^8$ cfu/ml). A cotton swab was placed in the suspension and streaked across the surface of the Muller-Hinton agar plate to cover the entire plate. All plates were placed in a 37° C. incubator for at least 24 hours. The external diameter of the biliary stent segments was ca. 3 mm. Zones of inhibition were measured the next day and are provided in Table 8.

TABLE 7

Zones of Inhibition with Minicycline/Riampin Coated Polyethylene Biliary Stents (mm)

| | Staphylococcus epidermidis | Staphylococcus aureus | Pseudomonas aeruginosa | Escherichia coli | Candida albicans | Enterococcus faecalis |
|---|---|---|---|---|---|---|
| Baseline | 41 | 35 | 12 | 18 | 5 | 24 |

EXAMPLE 8

PTFE-Collagen-M/R-OCA

In this example, 10 cm polytetrafluoroethylene (PTFE) biliary stents were used for treatment. A solution of 10 ml of

TABLE 8

Zones of Inhibition with Minicycline/Riampin Coated PTFE Biliary Stents (mm)

| | Staphylococcus epidermidis | Staphylococcus aureus | Pseudomonas aeruginosa | Escherichia coli | Candida albicans | Enterococcus faecalis |
|---|---|---|---|---|---|---|
| Baseline | 41 | 38 | 10 | 19 | 5 | 22 | glacial acetic acid with 500 mg of minocycline and 500 mg of rifampin was prepared at room temperature. 50 mg of collagen acid soluble collagen from New Zealand White rabbit skin (about 0.5% (w/v)) and 120 µl of glycerol were added to this solution at room temperature. The devices were immersed in this solution for 30 seconds and then placed under a dark well-ventilated fume hood for 5 hours. The second layer was applied under a well-ventilated fume hood by immersing the devices in a solution of 2-octyl cyanoacrylate for 5 seconds. After the second coating layer was applied, the devices were placed under a dark well-ventilated fume food for about 12 hours of drying.

EXAMPLE 9

PVC-Collagen-M/R-BCA

In this example, polyvinylchloride (PVC) oral endotracheal tubes were used for treatment. A solution of 10 ml of glacial acetic acid with 500 mg of minocycline and 500 mg of rifampin was prepared at room temperature. 50 mg of collagen acid soluble collagen from New Zealand White rabbit skin (about 0.5% (w/v)) and 120 µl of glycerol were added to this solution at room temperature. The devices were immersed in this solution for 30 seconds and then placed under a dark well-ventilated fume hood for 5 hours. The second layer was applied under a well-ventilated fume hood by immersing the devices in a solution of butyl cyanoacrylate for 5 seconds. After the second coating layer was applied, the devices were placed under a dark well-ventilated fume food for about 12 hours of drying.

Upon drying, the antimicrobial activity of the coated devices were measured by performing a modified Kirby-Bauer method. Devices were cut in one-centimeter segments. Five segments were used for baseline antimicrobial activity. Zones of inhibition were performed against *Staphylococcus epidermidis, Staphylococcus aureus, Pseudomonas aeruginosa, Escherichia coli, Candida albicans,* and *Enterococcus faecalis* according to Kirby-Bauer method. Each coated device segment was half embedded in the center of a Muller-Hinton agar plate that had been previously inoculated with individual organisms. Prior to placing the segments in agar, each organism was grown for 18 hours in trypticase soy broth to a concentration of 0.5 McFarland U ($10^8$ cfu/ml). A cotton swab was placed in the suspension and streaked across the surface of the Muller-Hinton agar plate to cover the entire plate. All plates were placed in a 37° C. incubator for at least 24 hours. The external radial diameter of endotracheal tube segments was ca. 6 mm. Zones of inhibition were measured the next day and are provided in Table 9.

TABLE 9

Zones of Inhibition with Minicycline/Riampin Coated PVC Endotracheal Tubes (mm)

| | *Staphylococcus epidermidis* | *Staphylococcus aureus* | *Pseudomonas aeruginosa* | *Escherichia coli* | *Candida albicans* | *Enterococcus faecalis* |
|---|---|---|---|---|---|---|
| Baseline | 48 | 35 | 18 | 25 | 18 | 28 |

This coating method provides broad-spectrum antimicrobial activity. Other applications include incorporation of other types of antimicrobial agents as well as non-antimicrobial compounds such as bone modulators on medical implants. This technique produces a biocompatible resilient coat, which has a slow release mechanism for drug delivery.

All patents and publication mentioned in this specification are indicative of the levels of those skilled in the art to which the invention pertains. All such patents and publications are herein incorporated by reference to the same extent as if each individual publication was specifically and individually indicated to be incorporated by reference.

The present invention, therefore, is well adapted to carry out the objects and attain the ends and advantages mentioned as well as other inherent therein. While presently preferred embodiments of the invention are given for the purpose of disclosure, numerous changes in the details will readily suggest themselves to those skilled in the art and which are encompassed within the spirit of the invention; and the scope of the appended claims.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of coating at least a portion of a medical device with a therapeutic agent comprising the steps of:
   forming a first composition by combining at least the following:
   a therapeutic agent,
   an acidic component,
   a matrix component selected from the group consisting of hide powder, collagen, gelatin, cartilage, tendon, ligament, bone, keratin, fibrin, albumin, globulin, hydroxylapatite, and any combination thereof; and,
   glycerol;
   applying said first composition to at least a portion of said medical device to form a first layer;
   forming a second composition comprising a cyanoacrylate; and,
   applying said second composition on said first layer to form a second layer.

2. The method of claim 1, further comprising the step of drying said first layer.

3. The method of claim 2, wherein said step of drying is performed in the dark.

4. The method of claim 1, further comprising the step of drying said second layer.

5. The method of claim 1, further comprising the steps of drying said first layer and drying said second layer.

6. The method of claim 1, wherein said matrix component is a combination of hide powder and collagen, said hide powder is added to achieve a 5% to 50% (w/v) concentration and said collagen is added to achieve a 0.1% to 20% (w/v) concentration in said first solution.

7. The method of claim 1, wherein said acid solution comprises a short chain monocarboxylic acid having a liquidity state below 90° C. and a pKa of 3 to 5.

8. The method of claim 1, wherein said acidic component is an acid solvent or acidic solution and said acid solvent or acidic solution is combined with said hide powder or collagen at a temperature range of 25° C. to 90° C. and mixed until a clear homogeneous solution is obtained.

9. The method of claim 1, wherein said glycerol is added such that the final concentration of glycerol is between 0.5% and 10%.

10. The method of claim 1, wherein said glycerol in said first composition is added after said therapeutic agent, said acidic component, and said matrix component.

11. The method of claim 1, wherein said step of applying said first composition to at least a portion of said medical device is selected from the group consisting of immersing the medical device in the first composition, spraying the first composition onto the medical device, pouring the first composition over the medical device, blotting the first composition on the medical device, smearing the first composition on the medical device, rolling the medical device in the first composition, brushing the first composition on the medical device, and any combination thereof.

12. The method of claim 1, wherein said cyanoacrylate is selected from the group consisting of methyl cyanoacrylate, ethyl cyanoacrylate, butyl cyanoacrylate, octyl cyanoacrylate, hexyl cyanoacrylate, decyl cyanoacrylate, methoxy ethyl cyanoacrylate, isoamyl cyanoacrylate, isopropyl cyanoacrylate and any combination thereof.

13. The method of claim 1, wherein said step of applying said second composition is selected from the group consisting of immersing the medical device in the second composition, spraying the second composition onto the medical device, pouring the second composition over the medical device, blotting the second composition on the medical device, smearing the second composition on the medical device, rolling the medical device in the second composition, brushing the second composition on the medical device, and any combination thereof.

14. The method of claim 1, further comprising the step of drying said first layer from about 1 hour to about 24 hours.

15. The method of claim 14, wherein said first layer is dried for about 16 hours.

16. The method of claim 1, further comprising the step of drying said second layer from about 5 minutes to about 18 hours.

17. The method of claim 16, wherein said second layer is dried for about 12 hours.

18. The method of claim 1, further comprising the step of applying a cyanoacrylate coat as a primer before said step of applying said first composition.

19. The method of claim 1, further comprising the step of controlling the viscosity of said second composition comprising a cyanoacrylate.

20. The method of claim 1, further comprising the step of controlling the temperature of said second composition comprising a cyanoacrylate.

21. The method of claim 1, further comprising the step of exposing the coating device to moisture after said step of applying said second composition on said first layer.

22. The method of claim 1, wherein said first composition comprises hide powder at a concentration of about 29% (w/v).

23. The method of claim 1, wherein said first composition comprises collagen at a concentration of about 0.5% (w/v).

24. The method of claim 1, wherein said first composition comprises glycerol at a concentration of about 1.25% (w/v).

25. The method of claim 1, wherein said therapeutic agent comprises a combination selected from the group consisting of:
at least one antibiotic and at least one antiseptic;
at least one antibiotic and at least one disinfectant;
at least one antiseptic and at least one disinfectant; and,
at least one antimicrobial agent.

26. The method of claim 1, wherein said therapeutic agent comprises at least one antimicrobial agent.

27. An implantable medical device comprising:
a body having one or more surfaces;
a first coating on at least a portion of said body, said first coating comprising:
glycerol,
a therapeutic agent,
an acidic component, and;
a matrix component selected from the group consisting of hide powder, collagen, gelatin, cartilage, tendon, ligament, bone, keratin, fibrin, albumin, globulin, hydroxylapatite, and any combination thereof;
a second coating on at least a portion of said first coating, said second coating comprising a cyanoacrylate.

28. The medical device of claim 27, wherein the therapeutic agent is an antimicrobial agent.

29. The medical device of claim 28 wherein said antimicrobial agent is selected from the group consisting of methylisothiazolone, thymol, α-terpineol, cetylpyridinium chloride, chloroxylenol, hexachlorophene, chlorhexidine and other cationic biguanides, methylene chloride, iodine, iodophores, triclosan, taurinamides, nitrofurantoin, methenamine, aldehydes, azylic acid, heavy metals, benzyl peroxide, alcohols, brilliant green, gentian violet, triacetin, salicylic acid, boric acid, carboxylic acids and their salts, erythromycin, nafcillin, cefazolin, imipenem, astreonam, gentamicin, tobramycin, streptomycin, amikacin, neomycin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, doxcycycline, tetracycline, tigecycline, oritavancin, daptomycin, dalbavancin, linezolid, temafloxacin, tosufloxacin, clinafloxacin, sulbactam, clavulanic acid, amphotericin B, fluconazole, miconazole, ravuconazole, posaconazole, clotrimazole, econazole, tioconazole, oxiconazole, bifonazole, isoconazole, fenticonazole, itraconazole, ketoconazole, voriconazole, terbinafine, caspofungin, anidulafungin, micafungin, nystatin, penicillins, cephalosporins, carbepenems, beta-lactams antibiotics, aminoglycosides, macrolides, lincosamides, glycopeptides, tetracylines, chloramphenicol, quinolones, fucidines, sulfonamides, trimethoprims, rifamycins, oxalines, streptogramins, oxazolidinones, lipepetides, ketolides, polyenes, azoles, echinocandines, and any combination thereof.

30. The medical device of claim 29 wherein said antimicrobial agent comprises heavy metal.

31. The medical device of claim 30, wherein said heavy metal is silver.

32. The medical device of claim 28 wherein said antimicrobial agent is a combination of two antimicrobial agents and is selected from the group consisting of chlorhexidine and methylisothiazolone; chlorhexidine and α-terpineol; thymol and chloroxylenol; thymol and methylisothiazolone; chlorhexidine and cetylpyridinium chloride; chlorhexidine and chloroxylenol; chlorhexidine, methylisothiazolone and thymol; methylisothiazolone and α-terpineol; minocycline and rifampin; and chlorhexidine, methylisothiazolone and α-terpineol.

33. The medical device of claim 28, wherein said antimicrobial agent is an antibiotic.

34. The medical device of claim 33, wherein said antibiotic is selected from the group consisting of penicillins, cephalosporins, carbepenems, other beta-lactams antibiotics, aminoglycosides, amphenicols, ansamycins, macrolides, lincosamides, glycopeptides, polypeptides, tetracylines, chloramphenicol, quinolones, fucidins, sulfonamides, sulfones, nitrofurans, diaminopyrimidines, trimethoprims, rifamycins, oxalines, streptogramins, lipopeptides, ketolides, polyenes, azoles, echinocandins, and any combination thereof.

35. The medical device of claim 27, wherein the therapeutic agent is an antimicrobial agent comprised of minocycline and rifampin.

36. The medical device of claim 27, wherein said therapeutic agent is selected from the group consisting of analgesics, anti-inflammatories, antidepressants, antiparasitics, anticancer drugs, anesthetics, antiallergics, anticoagulants, antidiabetics, antihypercholesterolemics, antihyperlipidemics, antineoplastics, calcium regulators, antihypertensives, antihypotensives, antihypothyroids, antihyperthyroids, antileukemics, antimanics, antiprotozoals, antivirals, reverse transcriptase inhibitors, antiamebics, antiarthritics, antirheumatics, antihemorrhagics, cardiotonics, contraceptives, antipsychotics, antispasmodics, antithrombotics, vasodilators, digestive aids, diuretics, enzymes, steroids, growth stimulators, immunosuppressants, immunomodulators, peristaltic stimulators, respiratory stimulators, and any combination thereof.

37. The medical device of claim 27, wherein the material comprising said medical device is selected from the group consisting of metals, metal alloys, carbon, carbon fibers, carbon polymer, ceramic, rubber, plastic, nylon, silicone, silicon, germanium, tin, gallium arsenide, polyurethane, polyethylene, polyvinyl chloride, polytetrafluoroethylene tetraphthalate, polyethylene tetraphthalate, polytetrafluoroethylene, polyglycolic acid, expanded polytetrafluoroethylene, latex, elastomers, polymers, polyglycolic acid, polylactide-co-glycolide, and polylactic acid, polymethyl methacrylate, latex, gelatin, collagen, albumin, globulin, and any combination thereof.

38. The medical device of claim 27, wherein the medical device is a catheter selected from the group consisting of peripherally insertable central venous catheters, dialysis catheters, long term tunneled central venous catheters, peripheral venous catheters, short-term central venous catheters, arterial catheters, pulmonary artery Swan-Ganz catheters, urinary catheters, long term non-tunneled central venous catheters, peritoneal catheters, and ventricular catheters.

39. The medical device of claim 27, wherein the medical device is selected from the group consisting of long term urinary devices, tissue bonding urinary devices, penile prostheses, vascular grafts, extravascular grafts, urinary stents, vascular catheter ports, wound drain tubes, drug delivery systems, neurotransmitters, epidural catheters, cerebrospinal fluid draining systems, hydrocephalus shunts, pacemaker systems, implantable stimulators, implantable infusion pumps, ventricular bypass assist devices, tissue expanders, implantable pulse generators, maxillofacial implants, mandibular implants, contraceptive tubal occlusion devices, contraceptive intrauterine devices, artificial anal sphincters, artificial urinary sphincters, vascular dilators, extravascular dilators, intravascular stents, extravascular stents, small joint replacements, temporary joint replacements, urinary dilators, heart valves, orthopedic implants, heart assist devices, mammary implants, dental devices, pacemakers, defibrillators, hip prostheses, knee prostheses, spinal prostheses, shoulder prostheses, joint prostheses, fracture fixation devices, external fixation pins, intramedullary nails, screws, plates, rods, and cages.

40. The medical device of claim 27, wherein said cyanoacrylate is selected from the group consisting of methyl cyanoacrylate, ethyl cyanoacrylate, butyl cyanoacrylate, octyl cyanoacrylate, hexyl cyanoacrylate, decyl cyanoacrylate, methoxy ethyl cyanoacrylate, isoamyl cyanoacrylate, isopropyl cyanoacrylate and any combination thereof.

41. The medical device of claim 27, wherein said therapeutic agent comprises a combination selected from the group consisting of:

at least one antibiotic and at least one antiseptic;

at least one antibiotic and at least one disinfectant;

at least one antiseptic and at least one disinfectant; and, at least one antimicrobial agent.

\* \* \* \* \*